US008298758B2

(12) United States Patent
Horikoshi et al.

(10) Patent No.: US 8,298,758 B2
(45) Date of Patent: Oct. 30, 2012

(54) METHOD OF MULTIPLEX MICROORGANISM DETECTION

(75) Inventors: Naoko Horikoshi, Tsuchiura (JP); Susumu Kawasaki, Tsukuba (JP); Yukio Okada, Tsuchiura (JP); Kazuko Takeshita, Tsuchiura (JP); Takashi Sameshima, Tsuchiura (JP); Shinichi Kawamoto, Tsukuba (JP); Kenji Isshiki, Tsukuba (JP)

(73) Assignees: Prima Meat Packers, Ltd., Tokyo (JP); National Agriculture and Food Research Organization, Tsukuba-shi (JP)

( * ) Notice: Subject to any disclaimer, the term of this patent is extended or adjusted under 35 U.S.C. 154(b) by 1244 days.

(21) Appl. No.: 10/584,393

(22) PCT Filed: Dec. 24, 2004

(86) PCT No.: PCT/JP2004/019340
§ 371 (c)(1),
(2), (4) Date: Nov. 21, 2006

(87) PCT Pub. No.: WO2005/064016
PCT Pub. Date: Jul. 14, 2005

(65) Prior Publication Data
US 2008/0014578 A1 Jan. 17, 2008

(30) Foreign Application Priority Data
Dec. 26, 2003 (JP) .................... 2003-435943

(51) Int. Cl.
*C12Q 1/68* (2006.01)
(52) U.S. Cl. ........................................ 435/6.1
(58) Field of Classification Search .............. None
See application file for complete search history.

(56) References Cited

U.S. PATENT DOCUMENTS

| | | | | |
|---|---|---|---|---|
| 5,589,335 A | * | 12/1996 | Kearney et al. | 435/6 |
| 6,011,148 A | * | 1/2000 | Bussey et al. | 536/25.4 |
| 6,468,743 B1 | * | 10/2002 | Romick et al. | 435/6 |

FOREIGN PATENT DOCUMENTS

| | | |
|---|---|---|
| EP | 0552571 A1 | 7/1993 |
| JP | 05-317033 | 12/1993 |
| JP | 06-165676 | 6/1994 |
| JP | 06-289016 | 10/1994 |
| JP | 09-500793 | 1/1997 |
| JP | 11-332599 | 12/1999 |
| JP | 2001-95576 | 4/2001 |
| JP | 2005-034121 | 2/2005 |
| KR | 2002 069 573 | 9/2002 |
| WO | 95/05461 | 2/1995 |

OTHER PUBLICATIONS

Hsih et al. (J Food Prot. Nov. 2001;64(11):1744-50).*
Buck et al ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
Aznar, et al., "On the Specificity of PCR Detection of Listeria monocytogenes in Food: a Comparison of Published Primers", System. Appl. Microbiol. 2002, 25(1):109-119.
Cocolin, et al., "A Multiplex-PCR Method to Detect Enterohemorrhagic (EHEC) and Enteropathogenic (EPEC) Escherichia coli in Artificially Contaminated Foods", Int. J. Hyg. Eviron. Health 2000, 203(2):159-164.
Supplementary European Search Report for the corresponding European national phase application No. 04807697.0 of the PCT Application No. PCT/JP2004/019340, actual completion of the European search Apr. 30, 2007; date of mailing May 9, 2007.
English Abstract for JP 2001-95576.
English Abstract for JP 11-332599.
English Abstract for JP 06-165676.
English Abstract for JP 06-289016.
Brasher C.W. et al., "Detection of Microbial Pathogens in Shellfish With Multiplex PCR," Current Microbiology, vol. 37, pp. 101-107, (1998).
Taguri T. et al., "The Simultaneous Detection Method of 18 Species of Food-born Pathogenic Bacteria by Multiplex PCR," Annual Report Nagasaki Prefectural Institute of Public and Environmental Sciences, vol. 48, pp. 43-56, (2002).
International Search Report for corresponding International Application No. PCT/JP2004/019340.
Michiko Miyahara et al., "Studies on Methods for Detection and Isolation of Pathogenic Bacterial in Vegetables and Fruits", Japanese Journal of Food Microbiology, vol. 19, No. 2, 47-55, 2002.

(Continued)

Primary Examiner — Christopher M. Babic
(74) Attorney, Agent, or Firm — Locke Lord LLP

(57) ABSTRACT

The present invention is to provide a multiple detection method that can detect contaminating microorganisms existing in foods, including pathogenic *Escherichia coli* O157, *Listeria monocytogenes* and *Salmonella* spp., with high sensitivity comparable or even superior to official methods, comprising the steps of amplifying a plural number of target genes with a single PCR reaction tube and analyzing the same. The following steps are performed consecutively: (A) a step of extracting DNA of the target microorganisms to be detected by treating with at least a lytic enzyme such as Achromopepidase and Lysozyme and/or bacteriocin having lytic activity such as Enterolysine, a surfactant and a protein denaturing agent; and (B) a step of mixing a specific primer to the target microorganisms to be detected to perform multiplex PCR. Further, it is preferable to add a step of culturing with a culture condition where 1 CFU/100 g microorganisms becomes $10^3$ CFU/ml or more after 18 to 48 h of culture, for example that the pH after culture becomes 5.1 or more, before the step of extracting DNA of the target microorganisms to be detected.

17 Claims, 1 Drawing Sheet

OTHER PUBLICATIONS

P.M. Fratamico et al., "Simultaneous detection of *Salmonella* ssp and *Escherichia coli* O157:H7 by multiplex PCR", Journal of Industrial Microbiology & Biotechnology, 21, 92-97, 1998.

Hsien-Yee Hsih et al., "Combination of Immunomagnetic Separation and Polymerase Chain Reaction for the Simultaneous Detection of *Listeria monocytogenes* and *Salmonella* ssp. in Food Samples", Journal of Food Protection, vol. 64, No. 11, 1744-1750, 2001.

M. Wagner et al., "A two step multiplex-seminested Polymerase Chain Reaction assay (m-sn PCR) for the simultaneous identification of four major foodborne pathogens", Milchwissenchaft 55 (9), 500-503, 2000.

V.K. Sharma et al., "Semi-automated fluorogenic PCR assays (Taq-Man) for rapid detection of *Escherichia coli* O157:H7 and other Shiga toxigenic *E. coli*", Molecular and Cellular Proges, 13, 291-302, 1999.

Mueen Aslam et al., "Development of a PCR-based assay to detect Shiga Toxin-producing *Escherichia coli, Listeria monocytogenes*, and *Salmonella* in milk", Food Microbiology, 20, 345-350, 2003.

English Abstract for JP 2001-95576, Date: Apr. 10, 2001.
English Abstract for JP 11-332599, Date: Dec. 7, 1999.
English Abstract for JP 06-165676, Date: Jun. 14, 1994.
English Abstract for JP 06-289016, Date: Oct. 18, 1994.

* cited by examiner

METHOD OF MULTIPLEX MICROORGANISM DETECTION

TECHNICAL FIELD

The present invention relates to a method for multiple microorganism detection that can detect microorganisms including pathogenic E. coli O157, Listeria monocytogenes and Salmonella spp. existing in foods, with high sensitivity comparable or even superior to official methods (KOTEI-HO: Japan), comprising the steps of amplifying a plurality of target genes with a single PCR reaction tube and analyzing the same.

BACKGROUND ART

Conventionally, methods of multiple microorganism detection using multiplex PCR are well known. For example the following methods have been reported: a method of multiple detection of bacteria of pathogenic Escherichia coli O157, Salmonella spp. and Listeria monocytogenes, targeting vegetables and fruits (for example, see non-patent document 1); a method of multiple detection of pathogenic Escherichia coli O157 and Salmonella spp. in foods (for example, see non-patent document 2); a method of multiple detection of various bacteria of pathogenic Escherichia coli O157, Salmonella spp., Listeria monocytogenes and Campylobacter spp., targeting milk (for example, see non-patent document 3); a method for multiple detection of Salmonella spp. and Listeria monocytogenes in foods (for example, see non-patent document 4); a method for multiple detection of Escherichia coli including pathogenic Escherichia coli O157, in foods (for example, see non-patent document 5); and a method for multiple detection of bacteria of pathogenic Escherichia coli O157, Salmonella spp. and Listeria monocytogenes, targeting milk (for example, see non-patent document 6). Further, primers for detecting Escherichia coli (for example, see patent document 1) and primers for detecting O-antigen of pathogenic Escherichia coli O157 (for example, see patent document 2) are known as primers for multiplex PCR.

On the other hand, as for methods for extracting DNAs of microorganisms, the following methods are known: a method using lytic enzyme Achromopeptidase and the like to mycobacterium such as tubercle bacilli (for example, see patent document 3); a method using lytic enzyme Achromopeptidase and the like to Gram negative bacteria and Gram positive bacteria (for example, see patent document 4); a method using proteinase K or Achromopeptidase and the like to Legionella (for example, see patent document 5); and a method using protein denaturant, reducing agent, surfactant, chelator and the like to Escherichia coli and the like (for example, see patent document 6).

Patent document 1: Japanese Laid-Open Patent Application No. 2001-95576
Patent document 2: Japanese Laid-Open Patent Application No. 11-332599
Patent document 3: Japanese Laid-Open Patent Application No. 6-165676
Patent document 4: Japanese Laid-Open Patent Application No. 9-500793
Patent document 5: Japanese Laid-Open Patent Application No. 5-317033
Patent document 6: Japanese Laid-Open Patent Application No. 6-289016
Non-patent document 1: Japanese Journal of Food Microbiology, Vol. 19, No. 2, 47-55, 2002
Non-patent document 2: Journal of Industrial Microbiology & Biotechnology, 21, 92-98, 1998
Non-patent document 3: Milchwissenschaft, 55(9), 500-503,
Non-patent document 4: Journal of Food Protection, Vol. 64, No. 11, 1744-1750, 2001
Non-patent document 5: Molecular and Cellular Probes, 13, 291-302, 1999
Non-patent document 6: Food Microbiology, 20, 345-350, 2003

DISCLOSURE OF THE INVENTION

Object to be Solved by the Present Invention

Methods for detecting one type of microorganism by PCR have been already established, while methods for detecting simultaneously plural microorganisms are being considered in the food sector but no methods sufficiently reliable have been established so far. The object of the present invention is to provide a method of multiple microorganism detection that can detect contaminating microorganisms including pathogenic Escherichia coli O157, Listeria monocytogenes and Salmonella spp. existing in foods, with high sensitivity comparable, or even superior to official methods, comprising the steps of amplifying a plurality of target genes with a single PCR reaction tube, and analyzing the same. In other words, it is to provide a method of multiple microorganism detection that can detect contaminating microorganisms including pathogenic Escherichia coli, Listeria monocytogenes and Salmonella spp., by using multiplex PCR, known as a PCR method using plural pairs of primers in combination, easily and with high sensitivity and good repeatability.

Means to Solve the Object (Culture)
Harmful pathogenic bacteria are set up to be "negative" in foods (not included in 25 g), and a comparable or even superior accuracy compared to that of official methods is required for the detection. Enrichment culture is essential to detect microorganisms that have been contaminated in minute amounts such as 1 CFU level in 25 g of food. When performing enrichment culture, usually, culture is conducted by using a selective medium for each target bacterium. However, in order to detect multiple microorganisms simultaneously, considerations were made to proliferate simultaneously plural microorganisms in one type of medium, even for enrichment culture. It is preferable to determine culture conditions leading to detection in the shortest possible time (for example, 24 hours or less), and therefore, the selection of medium becomes particularly important. It is relatively easy to proliferate bacteria simultaneously, when the target microorganisms belong to the same family or bacterial species of same genus, or if their growing properties are alike, but it is difficult for microorganisms of diverse types and having different growing properties. For example, when pathogenic Escherichia coli O157, Salmonella spp. and Listeria monocytogenes are the targets to be detected, there was a problem that among these three pathogenic bacteria, Listeria which grows at a low temperature, proliferates slower compared to Salmonella spp. and O157.

Therefore, medium having preferable nutrient source for Listeria, with low carbohydrate and high buffer ability were considered so that Listeria, in particular, can proliferate sufficiently even when other bacteria are contaminated. As a result, Listeria proliferated the fastest of the three contaminated bacteria, in medium No. 17 (tryptose 10 g, meat extract 5 g, yeast extract 5 g, sodium chloride 5 g, glucose 0.5 g, disodium phosphate 7 g, monopotassium phosphate 15 g/l L), compared to Trypto-soya broth or BHI (Brain Heart Infusion), BPW (Buffered peptone water), and *Salmonella* spp. and O157 proliferated faster than *Listeria*. This result suggested that medium No. 17 was preferable for detecting simultaneously these 3 types of bacteria.

(DNA)

At the time of PCR reaction, DNAs are extracted, and lytic operation is necessary for DNA extraction. Lysis of Gram positive bacteria is significantly difficult compared to that of Gram negative bacteria, as the main bacterial cell wall component is a thicker and higher-density peptide glycan layer. The present technique was difficult as *Listeria*, Gram positive bacteria, was to be detected simultaneously in addition to Gram negative bacteria including *Salmonella* spp. and O157. Further, from the point of view of extraction from foods, as food residues are various, it is difficult to determine one single lysis method. Particularly, in samples as represented by meat of livestock are high protein and high fat, and have individual difference, lysis is not performed at a constant efficiency, and thus, DNA extraction was difficult. Further consideration revealed that in some *Listeria*, cells were not disrupted (=DNAs could not be extracted) with only lysozyme, depending on the culture medium, such as Trypto-soya broth or Mueller Hinton Broth. It is estimated that culture conditions would change according to the type or the deterioration level of foods, even by using the same medium. Further, in some cases, as it is necessary to use media with better recovering ability, extraction methods wherein cells can be disrupted under any circumstances were necessary.

Boiling method and alkaline-SDS method are known as general DNA extraction method, while it was confirmed that *Listeria* could not be extracted with high sensitivity by the boiling method. SDS is known as a surfactant that is easy to use in DNA extraction, while as it is a strong PCR inhibitor, it is necessary to be removed completely after being used for extraction. For obtaining similar effects and results from an unskilled experimenter as from a skilled artisan, substances that affect the reaction even by a contamination at a low concentration, such as SDS, are not preferable, and SDS has been determined to be a dangerous factor that can be the cause of an extraction efficiency difference with that of a skilled artisan. Further, phenol and chloroform are organic solvent dangerous and harmful to human body and the purification level of DNA becomes better when performing treatment thereof. However, it can be easily estimated that there will be technical individual differences in extraction efficiency, and thus a constant sensitivity cannot be assured. Furthermore, as a particular waste liquid treatment is necessary, it can be said that it is not an extraction method suitable for examination in food manufacturing sites. Therefore, it was necessary to develop a method that is easy and safe so that it can be performed in food manufacturing sites, enabling DNA extraction even from high-protein foods as represented by meat of livestock, that can be operated easily by unskilled or skilled artisans, and that a constant DNA extraction efficiency (i.e. detection sensitivity) can be expected.

It was shown that bacteria could be lysed completely, by removing large food scraps by passing the culture solution through a 5 μm-filter, adding a lytic enzyme solution (mixed solution of Achromopeptidase and lysozyme), treating the mixture at 37° C. for 1 h, and adding a mixed solution of surfactant Polysorbate 20 (full name Polyoxyethylene (20) sorbitan monolaurate—commercially known as TWEEN® 20) and protein denaturant (Guanidine isothiocyanate). Moreover, it was shown that bacteria could be also lysed completely by using bacteriocin having lytic activity such as Enterolysine instead of Achromopeptidase. DNAs were extracted by removing insoluble fractions by centrifugation, and performing alcohol precipitation. It was shown that the following treatment order was extremely preferable: performing lysozyme treatment preferably prior to or simultaneously with Achromopeptidase; performing Enterolysine treatment preferably prior to or simultaneously with lysozyme treatment; then performing Polysorbate 20 (TWEEN® 20) treatment followed by Guanidine isothiocyanate treatment, or performing Polysorbate 20 (TWEEN® 20) treatment and Guanidine isothiocyanate treatment simultaneously. It was further shown that as Polysorbate 20 (TWEEN® 20) has high viscosity, it was difficult to add it separately, and thus adding it as a mixture was preferable.

Further, even phenol or chloroform treatment is not performed, protein being soluble to a level sufficient to be detected by PCR without problem can be removed by alcohol precipitation or according to the added level of DNA extraction solution (2 μl per 50 μl of PCR reaction solution). As Polysorbate 20 (TWEEN® 20) is also used in PCR reaction solution, there is less inhibition compared to SDS, and thus being easy to be used by unskilled experimenters. Moreover, these extraction methods can be applied for extraction of each bacterium alone, independently. Furthermore, the following methods have been tried: (1) Achromopeptidase alone; (2) lysozyme alone; (3) Enterolysine alone; (4) Achromopeptidase treatment followed by treatment with guanidine isothiocyanate+Polysorbate 20 (TWEEN® 20); (5) lysozyme treatment followed by guanidine isothiocyanate+Polysorbate 20 (TWEEN® 20); (6) Enterolysine treatment followed by treatment with guanidine isothiocyanate+Polysorbate 20 (TWEEN® 20); (7) proteinase K, (8) proteinase K treatment followed by treatment with guanidine isothiocyanate+Polysorbate 20 (TWEEN® 20); (9) guanidine isothiocyanate+Polysorbate 20 (TWEEN® 20) treatment; (10) guanidine isothiocyanate+Polysorbate 20 (TWEEN® 20)+heating treatment. However, the method comprising treatment with Achromopeptidase and lysozyme in combination, or treatment with Enterolysine and lysozyme in combination, followed by treatment with Polysorbate 20 (TWEEN® 20) and guanidine isothiocyanate was excellent from the point of view of Listeria extraction with high sensitivity, compared to any of the above methods.

(PCR Reaction)

Multiplex PCR was applied as a method for detecting simultaneously plural bacteria. For multiplex PCR method which is a PCR method performed by combining several primers, a pairing primer that do not mutually produce primer dimmer, or wherein their identification bands do not interfere or overlap each other, and having similar melting temperature were selected and used. It has been revealed that difference arises to the ease of reaction or detection limit according to the primer selection or mixing ratio. When performing multiplex PCR, it is necessary to adjust the primer mixing ratio in order to detect bands of 3 types of bacteria to be used in later determination, with a similar intensity in the electrophoresis image. When the 3 types of bacteria have the same DNA concentration (20 pg), it was adjusted so that the bands of 3 types of bacteria could be detected with a similar intensity. For example, when DNA consisting of base sequences shown by SEQ ID Nos: 1 to 6 is used as a primer, the most preferable mixing ratio of 6 primers was as follows: 120 nM each of *Salmonella* spp. primers, 100 nM each of *Listeria* primers; 80 nM each of O157 primers. Further, when DNA consisting of base sequences shown by SEQ ID Nos: 5 to 10 is used as a primer, the most preferable mixing ratio of 6 primers was: 60 nM each of *Salmonella* spp. primers; 60 nM each of *Listeria* primers; 240 nM each of O157 primers. Moreover, a mixing ratio with lower concentration, i.e. 30 nM each of *Salmonella* spp. primers, 25 nM each of *Listeria* primers and 20 nM each of O157 primers (when DNA consisting of base sequences shown by SEQ ID Nos: 1 to 6 is used); and 15 nM each of *Salmonella* spp. primers, 15 nM each of *Listeria* primers and 60 nM each of O157 primers (when DNA consisting of base sequences shown by SEQ ID Nos: 5 to 10 is used) were also investigated. However, as visual detection by electrophoresis was difficult though possible, the above concentration was revealed to be preferable.

Further, it is known that target genes can be amplified to approximately $10^{-8}$ M as final production level by PCR reaction. Normally, approximately 200 nM of primer is added to 1 bacterium in PCR reaction, while in case of multiple detection, it was revealed that this primer level is obviously excessive to be added to each bacterium. Particularly, in case of multiplex reaction, it is highly possible that only results of dominant reaction caused by generated products due to the excessive primer (including non-targeted product) are obtained. Thus, the relationship between the control of the final product level with the multiplex reaction was considered by controlling the primer level in PCR reaction. Naturally, as non-amplified products as represented by primer dimmer also consume primers in PCR reaction, it was revealed that although there is a lower limit of the concentration, more multiplex reactions could be achieved successively by determining the primer concentration to the minimum sensitivity of the detecting machine. In other words, by adjusting the lower limit primer concentration to the sensitivity of the detecting machine, detection of more microorganisms can be expected. By considering the detection machine limit for electrophoresis, fluorescent probe method, or capillary electrophoresis method, the reaction was to be conducted at approximately 50 nM or more, and detection of 3 types of pathogenic bacteria was confirmed. It is estimated that by increasing the detection machine sensitivity, this concentration can be set to a lower level, and thus, more targets can be detected at once. It was also revealed that if a more sensitive method for detecting amplification products is realized, by controlling the final product level in view of the above, simultaneous multiple detection by more Multiplex PCR can be realized.

In other words, the present invention relates to: (1) a method of multiple microorganism detection which is a method for detecting two or more microorganisms having different properties in foods, with high sensitivity comparable or even superior to official methods, by amplifying a plurality of target genes with a single PCR reaction tube and analyzing the same, comprising the following steps:
(A) a step for extracting DNA of the target microorganisms to be detected, by treating at least with a lytic enzyme and /or bacteriocin having lytic activity, a surfactant and a protein denaturant; and
(B) a step for performing Multiplex PCR by mixing a primer specific to the target microorganisms to be detected; (2) the method of multiple microorganism detection according to (1), wherein a step to culture microorganisms under a culture condition where 1 CFU/100 g microorganisms become $10^3$ CFU/ml or more after 24 h of culture, is included prior to the step of extracting DNA of the target microorganisms to be detected; (3) the method of multiple microorganism detection according to (1) or (2), wherein the two or more microorganisms with different properties comprise *Listeria monocytogenes*; (4) the method of multiple microorganism detection according to (3), wherein the specific primer is a primer consisting of base sequences shown by SEQ ID Nos: 5 and 6; (5) the method of multiple microorganism detection according to (1) or (2), wherein the two or more microorganisms with different properties comprise pathogenic *Escherichia coli* O157; (6) the method of multiple microorganism detection according to (5), wherein the specific primer is a primer consisting of base sequences shown by SEQ ID Nos: 1 and 2, or SEQ ID Nos: 7 and 8; (7) the method of multiple microorganism detection according to (1) or (2), wherein the two or more microorganisms with different properties comprise *Salmonella* spp.; (8) the method of multiple microorganism detection according to (7), wherein the specific primer is a primer consisting of base sequences shown by SEQ ID Nos: 3 and 4, or SEQ ID Nos: 9 and 10.

Moreover, the present invention relates to: (9) the method of multiple microorganism detection according to any one of (1) to (8), wherein the microorganisms are cultured in a culture condition where the pH after culture becomes 5.1 or more; (10) the method of multiple microorganism detection according to any one of (1) to (9), wherein the microorganisms are cultured in a medium with glucose concentration of 0.15% or less, and/or in a medium with concentration of phosphate-buffer solution of 50 mM or more or in a medium with a buffer ability similar as that with concentration of phosphate-buffer solution of 50 mM or more; (11) the method of multiple microorganism detection according to any one of (1) to (10), wherein the extraction is performed after treating with a lytic enzyme and/or bacteriosin having a lytic activity, further treating with a surfactant and a protein denaturant, removing insoluble fractions by centrifugation, and by depositing DNA by alcohol precipitation; (12) the method of multiple microorganism detection according to any one of (1) to (11), wherein the lytic enzyme is Achromopeptidase and/or lysozyme; (13) the method of multiple microorganism detection according to any one of (1) to (12), wherein bacteriosin having lytic activity is Enterolysine; (14) the method of multiple microorganism detection according to any one of (1) to (13), wherein the surfactant is ethyleneoxide condensate of sorbitan monolaurate; (15) the method of multiple microorganism detection according to any one of (1) to (14), wherein the protein denaturant is Guanidine isothiocyanate; (16) the method of multiple microorganism detection according to any one of (1) to (15), wherein Multiplex PCR is performed by combining DNA consisting of base sequences shown by SEQ ID NOs: 1 to 6 at a total concentration of 750 nM or less as a primer; (17) the method of multiple microorganism detection according to any one of (1) to (15), wherein Multiplex PCR is performed by combining DNA consisting of base sequences shown by SEQ ID NOs: 5 to 10 at a total concentration of 750 nM or less as a primer; (18) the method of multiple microorganism detection according to any one of (1) to (17), wherein the food is edible meat or processed meat product.

EFFECT OF THE PRESENT INVENTION

According to the present invention, microorganisms existing in foods, including pathogenic *Escherichia coli* O157, *Listeria monocytogenes* and *Salmonella* spp., can be detected easily with high sensitivity comparable or even superior to official methods, by amplifying a plurality of target genes with a single PCR reaction tube and analyzing the same.

BEST MODE OF CARRYING OUT THE INVENTION

The method of multiple microorganism detection of the present invention is not particularly limited as long as it is a method for detecting two or more microorganisms with different properties in food including edible meat, processed meat products, milk and vegetables, at a sensitivity comparable or even superior to official methods, by amplifying a plurality of target genes with a single PCR reaction tube and analyzing the same, comprising the following steps: (A) a step for extracting DNA of the target microorganisms to be detected, by treating at least with a lytic enzyme and/or bacteriocin having lytic activity, a surfactant and a protein denaturant; and (B) a step for performing Multiplex PCR by mixing a primer specific to the target microorganisms to be detected. However, it is preferable that a step to culture microorganisms under a culture condition where 1 CFU/100 g microorganisms become $10^3$ CFU/ml or more after 24 h of culture, is included prior to the above step (A)for extracting DNA of the target microorganisms to be detected. Further, target microorganisms to be detected are not limited as long as they are contaminating microorganisms in foods, and specifically include, *Listeria monocytogenes*, pathogenic *Escherichia coli* O157, *Salmonella* spp., *Campylobacter* spp., *Vibrio parahaemolyticus, Staphylococcus aureus, Yersinia, Coliform* bacteria, *Bacillus cereus, Vibrio cholerae, Shigella, Clostridium botulinum*. Further, official methods relate to the methods described in "Guidance for food hygiene inspection" (Japan Food Hygiene Association, 1990), and a specific example is described in Example 9.

According to the multiple microorganism detection method of the present invention, it is possible to detect microorganisms that have been contaminated in minute amounts such as 1 CFU level in 25 g of food, and in the multiple microorganism detection method of the present invention, the culturing process of the contaminating microorganisms in food is very important. As for culture conditions of enrichment culture of contaminating microorganisms in food, a culture condition where 1 CFU/100 g microorganism become $10^3$ CFU/ml or more after 48 h of culture, preferably after 30 h of culture, more preferably after 24 h of culture, and most preferably after 18 h of culture can be exemplified. It is further preferable to culture under a culture condition where the pH after culture becomes 5.1 or more using a medium with buffer ability, or to culture in a medium with glucose concentration of 0.15% or less, and/or in a medium with concentration of phosphate-buffer solution of 50 mM or more or in a medium with a buffer ability similar as that with concentration of phosphate-buffer solution of 50 mM or more. As for buffer solution other than phosphate buffer solution, citrate buffer solution, acetate buffer solution, lactate buffer solution, tartrate buffer solution, malate buffer solution, tris buffer solution, MOPS buffer solution and MES buffer solution can be exemplified.

In the multiple detection method of the present invention, the process for extracting DNA of contaminating microorganisms in foods which have been cultured and proliferated is indispensable. The DNA extraction process is not particularly limited as long as it is a process for extracting DNA of target microorganisms to be detected, by treating at least with a lytic enzyme and/or bacteriocin with lytic activity, a surfactant and a protein denaturant, while a method for depositing and extracting DNA by alcohol precipitation after treating with a lytic enzyme and/or bacteriocin with lytic activity, treating with a surfactant and a protein denaturant, and removing insoluble fractions by centrifugation can be preferably exemplified. Examples of the above lytic enzymes include: Achromopeptidase, lysozyme, proteinase K, chitosanase, chitinase, β-1,3-Glucanase, Zymolyase and Cellulase. Examples of bacteriocin having lytic activity include Enterolysine and helveticine. One or more of these can be used, while Achromopeptidase, lysozyme, Enterolysine, or a combination thereof, for example simultaneous use of Achromopeptidase and lysozyme, simultaneous use of Enterolysine and lysozyme, can be preferably exemplified. As for the above surfactants, anion surfactant, cation surfactant, amphoteric surfactant, nonionic surfactant can be exemplified. Among these, ethylene oxide condensate of sorbitan monolaurate which is a nonionic surfactant, more specifically Polysorbate 20 (TWEEN® 20), can be preferably exemplified. As for the above protein denaturants, guanidine isothiocyanate, urea, guanidine hydrochloride, trichloroacetate, SDS, Triton X-100 and deoxycholate can be exemplified. One or more of these can be used, while guanidine isothiocyanate is preferable from the view point of bacteriolysis or easy handling. Extract/deposit of DNA from lysates can be performed by commonly known methods such as removing insoluble fractions by centrifugation, and then performing alcohol precipitation.

In the multiple detection method of the present invention, a process comprising the steps of mixing the above extracted DNA and a primer specific to target microorganisms to be detected, to perform multiplex PCR, is indispensable. As for primers used, it is preferable to select a primer specific to target microorganisms to be detected, which is a pairing primer having similar melting temperature that do not mutually produce primer dimmer, or wherein their identification bands do not interfere or overlap each other. Further, it is preferable to adjust the mixing ratio of the primers so that bands appearing in electrophoresis used for the subsequent determination, can be detected with similar intensity. For example, as for primer set specific for pathogenic *Escherichia coli* O157, DNA consisting of base sequences shown by SEQ ID NOs: 1 and 2, SEQ ID NOs: 7 and 8, SEQ ID NOs: 11 and 12, SEQ ID NOs: 13 and 14, etc.; as for primer set specific for *Salmonella* spp., DNA consisting of base sequences shown by SEQ ID NOs: 3 and 4, SEQ ID NOs: 9 and 10, SEQ ID NOs: 15 and 16, etc.; as for primer set specific to *Listeria monocytogenes*, DNA consisting of base sequences shown by SEQ ID NOs: 5 and 6, SEQ ID NOs: 17 and 18, SEQ ID NOs: 19 and 20, etc. can be exemplified respectively, and these can be used in combinations. Among these, the combination of DNA consisting of base sequences shown by SEQ ID NOs: 1 to 6, or SEQ ID NOs: 5 to 10 is the most preferable, and in this case, it is preferable to mix primers at a total concentration of 750 nM or less. When SEQ ID NOs: 1 to 6 are used, the preferable mixing ratio of the 6 primers is: 120 nM each of *Salmonella* spp. primers, 100 nM each of *Listeria* primers, 80 nM each of O157 primers, and when SEQ ID NOs: 5 to 10 are used, the preferable mixing ratio is: 60 nM each of *Salmonella* spp. primers, 60 nM each of *Listeria* primers, and 240 nM each of O157 primers.

The detection method after PCR can be performed by, for example, electrophoresis, fluorescent probe method, capillary electrophoresis method, or quantitative PCR method. Particularly, in case of quantitative PCR, it can be detected by using DNA consisting of base sequences shown by SEQ ID NOs: 5 to 10 as primer, and by using DNA consisting of base sequences shown by SEQ ID NOs: 21 to 23 as fluorescent probe.

In the following, the present invention will be explained more in detail, while the technical scope of the present invention is not limited to these exemplifications.

EXAMPLE 1

(Simultaneous Culture in an Existing Medium)

*Escherichia coli* O157:H7 ATCC43894, *Salmonella* spp. *enteritidis* IFO3313 and *Listeria monocytogenes* ATCC49594 were used for pathogenic *Escherichia coli*, *Salmonella* spp. and *Listeria monocytogenes*, respectively. Further, as for meat-derived bacteria, 4 strains, *Pseudomonas fragi, Citrobacter freundii, Lactobacillus viridescens* and *Leuconostoc mesenteroides* were used. As for a test medium, 2 media, Trypto-soya broth (TSB; Nissui Pharmaceutical) and Buffered Peptone Water (BPW; peptone 10 g, sodium chloride 5 g, sodium hydrogenphosphate 3.5 g, potassium dihydrogenphospate 1.5 g/1 L) were used.

Meat-derived bacteria, and 1 CFU/100 ml each of pathogenic *Escherichia coli* O157, *Salmonella* spp., and *Listeria monocytogenes* were inoculated in the test medium where each bacterium becomes $10^4$ CFU/100 ml. After culturing at 35° C., counts of general viable cells, O157, *Salmonella* spp. and *Listeria* were counted chronologically. As for general viable cell counts, the total colony counts were measured after culturing at 35° C. for 48 h by using a standard agar medium (Nissui Pharmaceutical); as for O157 counts, the *Escherichia coli*-like colony counts after culturing at 35° C. for 24 h by using desoxycholate agar medium (Nissui Pharmaceutical); as for *Salmonella* spp. counts, the *Salmonella* spp.-like colony counts after culturing at 35° C. for 24 h by using MLCB agar medium (Nissui Pharmaceutical); as for *Listeria* counts, the *Listeria*-like colony counts after culturing at 35° C. for 48 h by using LCAM agar medium (Merck) were measured, respectively. The results are shown in FIG. 1. As a result, particularly the proliferation of *Listeria monocytogenes* was weak in any of the medium. By measuring the pH of the culture solution, decrease of pH was confirmed.

EXAMPLE 2

(Influence of Buffer Ability and Sugar Concentration of the Medium)

As it was thought that the weak proliferation of *Lysteria monocytogenes* in Example 1 was due to the decrease of pH of the medium after culture, the influence of buffer ability and sugar concentration of the medium on the proliferation of each bacterium was investigated. Disodium phosphate and monopotassium phosphate were added to the base medium (tryptose 10 g, meat extract 5 g, yeast extract 5 g, sodium chloride 5 g/1 L) to adjust the phosphate concentration from 15 mM to 200 mM (pH 6.3), and glucose was added by changing the concentration from 0% to 0.25% to prepare the test medium. Meat-derived bacteria and 1 CFU/100 ml each of pathogenic *Escherichia coli* O157, *Salmonella* spp. and *Listeria moncytegenes*, used in Example 1, were inoculated in each test medium where each of these becomes $10^4$ CFU/ml. After culturing at 35° C., counts of general viable cells, O157, *Salmonella* spp. and *Listeria*, and the pH levels were measured, 18, 24, 30 and 48 h later. The results are shown in Table 1

As a result, by using a medium with glucose concentration of 0.15% or less, or a medium with phosphate concentration of 50 mM or more, or a medium maintaining the pH after culture at 5.1 or more, all of pathogenic *Escherichia coli* O157, *Salmonella* spp. and *Listeria monocytogenes* proliferated to 103 CFU/ml or more (cell counts necessary for detection by PCR) by culturing for 18 h or more. For the tests thereafter, medium No. 17 of Table 1 (tryptose 10 g, meat extract 5 g, yeast extract 5 g, sodium chloride 5 g, glucose 0.5 g, disodium phosphate 7 g, monopotassium phosphate 15 g/1 L) was selected. As for medium components, nitrogen sources other than tryptose, meat extract or yeast extract, carbon sources other than glucose, substances with buffer ability other than phosphate are also effective according to the existing environment or damage level of the bacteria to be detected. Further, it was more preferable to add inorganic salts, pyruvic acid or pyruvate salt, or surfactants such as Polysorbate (TWEEN®) as substances promoting proliferation.

TABLE 1

| No. | Phosphate concentration (mM) | Glucose concentration (%) | General viable cell counts (CFU/ml) | O157 counts (CFU/ml) | *Salmonella* spp. counts (CFU/ml) | *Listeria* counts (CFU/ml) | pH | application |
|---|---|---|---|---|---|---|---|---|
| 1 | 15 | 0 | $2.4 \times 10^8$ | $1.4 \times 10^7$ | $6.2 \times 10^6$ | $2.0 \times 10^6$ | 5.99 | OK |
| 2 |  | 0.5 | $1.6 \times 10^8$ | $1.1 \times 10^7$ | $5.6 \times 10^6$ | $1.5 \times 10^6$ | 5.97 | OK |
| 3 |  | 1.0 | $3.0 \times 10^8$ | $5.7 \times 10^6$ | $4.3 \times 10^6$ | $4.7 \times 10^6$ | 5.62 | OK |
| 4 |  | 1.5 | $2.8 \times 10^8$ | $1.4 \times 10^5$ | $3.0 \times 10^5$ | $3.0 \times 10^4$ | 5.11 | OK |
| 5 |  | 2.0 | $3.2 \times 10^8$ | $5.1 \times 10^4$ | $9.1 \times 10^2$ | $6.1 \times 10^2$ | 4.79 | NG |
| 6 |  | 2.5 | $3.9 \times 10^8$ | $2.3 \times 10^4$ | $1.2 \times 10^3$ | 10 | 4.58 | NG |
| 7 | 30 | 0 | $2.1 \times 10^8$ | $3.2 \times 10^7$ | $5.1 \times 10^6$ | $6.2 \times 10^6$ | 6.13 | OK |
| 8 |  | 0.5 | $1.8 \times 10^8$ | $2.7 \times 10^7$ | $4.9 \times 10^6$ | $5.9 \times 10^6$ | 6.10 | OK |
| 9 |  | 1.0 | $4.4 \times 10^8$ | $2.0 \times 10^7$ | $4.8 \times 10^6$ | $3.0 \times 10^6$ | 5.94 | OK |
| 10 |  | 1.5 | $3.1 \times 10^8$ | $4.3 \times 10^6$ | $7.1 \times 10^6$ | $1.6 \times 10^6$ | 5.71 | OK |
| 11 |  | 2.0 | $6.8 \times 10^8$ | $4.8 \times 10^5$ | $2.4 \times 10^4$ | $6.9 \times 10^3$ | 5.40 | OK |
| 12 |  | 2.5 | $5.7 \times 10^8$ | $4.7 \times 10^5$ | $1.6 \times 10^4$ | $3.0 \times 10^2$ | 5.03 | NG |
| 13 | 50 | 0.5 | $1.1 \times 10^8$ | $2.4 \times 10^7$ | $5.2 \times 10^6$ | $6.1 \times 10^6$ | 6.12 | OK |
| 14 |  | 2.5 | $3.9 \times 10^8$ | $1.1 \times 10^7$ | $5.0 \times 10^4$ | $3.4 \times 10^4$ | 5.62 | OK |
| 15 | 100 | 0.5 | $3.2 \times 10^8$ | $2.5 \times 10^7$ | $5.1 \times 10^5$ | $5.2 \times 10^6$ | 6.10 | OK |
| 16 |  | 2.5 | $6.2 \times 10^8$ | $2.0 \times 10^7$ | $4.2 \times 10^6$ | $4.5 \times 10^6$ | 6.02 | OK |
| 17 | 150 | 0.5 | $4.4 \times 10^8$ | $4.1 \times 10^7$ | $5.4 \times 10^6$ | $5.8 \times 10^6$ | 6.17 | OK |
| 18 |  | 2.5 | $9.5 \times 10^8$ | $3.2 \times 10^7$ | $5.1 \times 10^6$ | $8.0 \times 10^6$ | 6.22 | OK |
| 19 | 200 | 0.5 | $1.2 \times 10^8$ | $3.2 \times 10^7$ | $5.1 \times 10^6$ | $5.8 \times 10^6$ | 6.17 | OK |
| 20 |  | 2.5 | $8.4 \times 10^7$ | $3.8 \times 10^7$ | $6.8 \times 10^6$ | $9.0 \times 10^6$ | 6.15 | OK |

EXAMPLE 3

(DNA Extraction Method 1)

Each bacteria of pathogenic *Escherichia coli* O157, *Salmonella* spp. and *Listeria monocytogenes* were inoculated to 10 ml of medium No. 17, and cultured at 35° C. for 18 h. Each culture solution was taken to a 1 ml-tube, respectively, centrifuged at 15,000 r.p.m for 5 min to collect bacteria. Lytic enzyme solution {mixed solution of 10 μl of 20 mg/ml Achromopeptidase and 10 μl of 20 mg/ml Lysozyme, and 180 μl of TE buffer [10 mM Tris (hydroxymethyl) aminomethane-hydrochloric acid buffer solution containing 1 mM EDTA, pH 8]} was added, treated at 37° C. for 1 h. Then, 300 μl of lysing agent (4 M guanidine isothiocyanate solution supplemented with 1 to 2% of Polysorbate 20 (TWEEN® 20) was added to dissolve bacteria completely. By observing this solution with a light microscope, it was confirmed that lysis was sufficiently performed. The solution was centrifuged at 15,000 r.p.m for 5 min and 400 µl of the supernatant was transferred to another tube. After precipitating DNA in the lysate with isopropanol, the resultant was centrifuged, and thus, the intended DNA was obtained. Further, by using Enterolysine instead of Achromopeptidase, it was confirmed that lysis was sufficiently performed, similarly.

EXAMPLE 4

(DNA Extraction Method 2)

Similarly, each bacteria of pathogenic *Escherichia coli* O157, *Salmonella* spp. and *Listeria monocytogenes* were inoculated to 10 ml of medium No. 17, and cultured at 35° C. for 18 h. Each culture solution was taken to a 1 ml-tube, respectively, centrifuged at 15,000 r.p.m for 5 min to collect bacteria. 500 µl of lytic agent (4 M guanidine isothiocyanate solution supplemented with 1 to 2% of Polysorbate 20 (TWEEN® 20) was added to the collected bacteria to dissolve collected substances. The resultant solution was heated at 100° C. for 10 min. and ice cooled for 5 min. By observing this solution with a light microscope, it was confirmed that pathogenic *Escherichia coli* O157 and *Salmonella* spp. were lysed, while the lysis level of *Listeria monocytogenes* was a little lower compared with that of the DNA extraction method of Example 3. Further, lysis of *Listeria monocytogenes* lysate was performed by adding the following: 1) a solution to which a mixed solution of 10 µl of 20 mg/ml Achromopeptidase and 190 µl of TE buffer was added to the collected bacteria, and treated at 37° C. for 1 h; 2) a solution to which a mixed solution of 10 µl of 20 mg/ml of Lysozyme and 190 µl of TE buffer was added to the collected bacteria, and treated at 37° C. for 1 h; 3) a solution to which a mixed solution of 10 µl of Enterolysine and 190 µl of TE buffer was added to the collected bacteria, and treated at 37° C. for 1 h; 4) a solution to which 300 µl of lysing agent (4 M guanidine isothiocyanate solution supplemented with 1 to 2% of Polysorbate 20 (TWEEN® 20) was added to the above 1) solution and mixed; 5) a solution to which 300 µl of lysing agent (4 M guanidine isothiocyanate solution supplemented with 1 to 2% of Polysorbate 20 (TWEEN® 20) was added to the above 2) solution and mixed; 6) a solution to which 300 µl of lysing agent (4 M guanidine isothiocyanate solution supplemented with 1 to 2% of Polysorbate 20 (TWEEN® 20) was added to the above 3) solution and mixed; 7) a solution to which a mixed solution of 1 µl of 20 mg/ml proteinase K1 and 200 µl of TE buffer was added to the collected bacteria, and treated at 37° C. for 1 h; 8) a solution to which 300 µl of lysing agent (4 M guanidine isothiocyanate solution supplemented with 1 to 2% of Polysorbate 20 (TWEEN® 20)) was added to the above 7) solution and mixed; 9) a solution to which 500 µl of lysing agent (4 M guanidine isothiocyanate solution supplemented with 1 to 2% of Polysorbate 20 (TWEEN® 20) was added to the collected bacteria and mixed. The resultants were observed with a light microscope. For all of these, the lysis level of *Listeria monocytogenes* was lower compared with that of DNA extraction method of Example 3.

EXAMPLE 5

(Determination of PCR Reaction Condition)

PCR reaction was performed by using the DNA extraction solution obtained in Example 3. For PCR, 1 set of primers specific to target microorganisms to be detected was respectively used from the following primers.

SEQ ID NO: 1:  GGC GGA TTA GAC TTC GGC TA

SEQ ID NO: 2:  CGT TTT GGC ACT ATT TGC CC

SEQ ID NO: 3:  GGG AGT CCA GGT TGA CGG AAA ATT T

SEQ ID NO: 4:  GTC ACG GAA GAA GAG AAA TCC GTA CG

SEQ ID NO: 5:  CGG AGG TTC CGC AAA AGA TG

SEQ ID NO: 6:  CCT CCA GAG TGA TCG ATG TT

SEQ ID NO: 7:  ATC ATT GAC GAT TGT AGC ACC

SEQ ID NO: 8:  ACA TGA GGA GCA TTA ACT TCG

SEQ ID NO: 9:  GGG TCG TTC TAC ATT GAC AG

SEQ ID NO: 10: TTC CCT TTC CAG TAC GCT TC

SEQ ID NO: 11: GTA TTT GGA GAC ATG GGA GC

SEQ ID NO: 12: ACT AAT GAC ACG ATT CGT TCC

SEQ ID NO: 13: CGG ACA GTA GTT ATA CCA C

SEQ ID NO: 14: CTG CTG TCA CAG TGA CAA A

SEQ ID NO: 15: AGC TTT GGT CGT AAA ATA GGG

SEQ ID NO: 16: GAT GCC CAA AGC AGA GAG AT

SEQ ID NO: 17: CAA ACT GCT AAC ACA GCT ACT

SEQ ID NO: 18: GCA CTT GAA TTG CTG TTA TTG

SEQ ID NO: 19: ACC AAT GGG ATC CAC AAG A

SEQ ID NO: 20: GAG CTG AGC TAT GTG CGA T

The PCR solution was made to be a total of 50 µl by adding 5 µl of 10× Buffer, 4 µl of dNTP solution, 0.5 µl of UNG, 0.25 µl of AmpliTaq Gold, 10 µl of MgCl$_2$ (all from Applied Biosystems Japan) primers and 2 µl solution of DNA extraction to distilled water. The reaction condition is: maintaining for 2 min at 50° C., allowing to react at 95° C. for 10 min, repeating 40 times the cycle of 95° C./20 sec, 60° C./30 sec, 72° C./30 sec, maintaining for 7 min at 72° C. and storing at 4° C. PCR products were confirmed by 2.5% agarose gel electrophoresis. When combining DNA consisting of base sequences shown by SEQ ID NOs: 1 to 6, the most ideal primer mixing ratio was: 80 nM each of pathogenic *Escherichia coli* O157 primer (SEQ ID NOs: 1, 2); 120 nM each of *Salmonella* spp. primer (SEQ ID NOs: 3, 4); 100 nM each of *Listeria monocytogenes* primer (SEQ ID NOs: 5, 6). For example, a mixing ratio with low concentration, i.e. 20 nM each of pathogenic *Escherichia coli* O157 primers; 30 nM each of *Salmonella* spp. primers; 25 nM each of *Listeria monocytogenes* primers was also investigated, while the visual detection by agarose electrophoresis was somewhat difficult though possible. Further, when DNAs consisting of base sequences shown by SEQ ID Nos: 5 to 10 was used, the most ideal primer mixing ratio were: 240 nM each of pathogenic *Escherichia coli* O157 primers (SEQ ID NOs: 7, 8); 60 nM each of *Salmonella* spp. primers (SEQ ID NOs: 9, 10); 60 nM each of *Listeria monocytogenes* primer (SEQ ID NOs: 5, 6). Furthermore, it was revealed that pathogenic *Escherichia coli* O157 primers (SEQ ID NOs: 11, 12; or SEQ ID NOs: 13, 14), *Salmonella* spp. primers (SEQ ID NOs: 15, 16) and *Listeria monocytogenes* primers (SEQ ID NOs: 17, 18; SEQ ID NOs: 19, 20) could be used by adjusting the mixing ratio, respectively.

Moreover, in the combination of SEQ ID NOs: 5 to 10, it was revealed that it could be detected by using a probe in which SEQ ID Nos: 21 to 23 specific to the inner sequences are labeled with a fluorescent dye, by detection method such as quantitative PCR or hybridization.

SEQ ID NO: 21: CGG ATG ATT TGT GGC ACG AGA AA

SEQ ID NO: 22: TCT GGC ATT ATC GAT CAG TAC CAG CC

SEQ ID NO: 23: AGT TCA AAT CAT CGA CGG CAA CCT CGG A

EXAMPLE 6

(Confirmation of Reaction Specificity)
4 strains of pathogenic *Escherichia coli* O157, 4 strains of *Salmonella* spp., 10 strains of *Listeria monocytogenes*, 4 strains of *Escherichia coli* other than pathogenic *Escherichia coli* O157, and 4 strains of *Listeria* other than *Listeria monocytogenes*, shown in Table 2 were used to confirm the specificity. Each bacterium was cultured at 35° C. for 18 h with Trypto-soya broth (Nissui Pharmaceutical), and as method 1, among the DNA extractions of Example 3, the extraction method using Achromopeptidase and lysozyme as lytic enzyme was performed, and among the PCR reactions of Example 5, a method using the combination of SEQ ID NOs: 1 to 6 was performed. As method 2, among the DNA extractions of Example 3, the extraction method using Enterolysine and lysozyme as lytic enzyme was performed, and among the PCR reactions of Example 5, a method using the combination of SEQ ID NOs: 5 to 10 was performed. By confirming the result of PCR reactions by 2.5% agarose gel electrophoresis, bands were detected at predetermined places of the electrophoresis image for pathogenic *Escherichia coli* O157, *Salmonella* spp. and *Listeria monocytogenes*, and these bacteria were shown to be positive. On the other hand, for *Escherichia coli* other than pathogenic *Escherichia coli* O157, and *Listeria* other than *Listeria monocytogenes*, no band was detected and the bacteria were shown to be negative, and it was confirmed that there was no problem to the specificity. The results are shown in Table 2.

TABLE 2

|  | Bacteria | Results Method 1 | Method 2 |
|---|---|---|---|
| 1-1 | *Escherichia coli* O157:H7 | positive | positive |
| 1-2 | *Escherichia coli* O157:H7 | positive | positive |
| 1-3 | *Escherichia coli* O157:H7 | positive | positive |
| 1-4 | *Escherichia coli* O157:H7 | positive | positive |
| 2-1 | *Salmonella Typhimurium* | positive | positive |
| 2-2 | *Salmonella Enteritidis* | positive | positive |
| 2-3 | *Salmonella Enteritidis* | positive | positive |
| 2-4 | *Salmonella* sp. | positive | positive |
| 3-1 | *Listeria monocytogenes* | positive | positive |
| 3-2 | *Listeria monocytogenes* | positive | positive |
| 3-3 | *Listeria monocytogenes* | positive | positive |
| 3-4 | *Listeria monocytogenes* | positive | positive |
| 3-5 | *Listeria monocytogenes* | positive | positive |
| 3-6 | *Listeria monocytogenes* | positive | positive |
| 3-7 | *Listeria monocytogenes* | positive | positive |
| 3-8 | *Listeria monocytogenes* | positive | positive |
| 3-9 | *Listeria monocytogenes* | positive | positive |
| 3-10 | *Listeria monocytogenes* | positive | positive |
| 4-1 | *Listeria welshimeri* | negative | negative |
| 4-2 | *Listeria innocua* | negative | negative |
| 4-3 | *Listeria ivanovii* | negative | negative |
| 4-4 | *Listeria seeligeri* | negative | negative |

TABLE 2-continued

|  | Bacteria | Results Method 1 | Method 2 |
|---|---|---|---|
| 5-1 | *Escherichia coli* O152 | negative | negative |
| 5-2 | *Escherichia coli* | negative | negative |
| 5-3 | *Escherichia coli* | negative | negative |
| 5-4 | *Escherichia coli* | negative | negative |

EXAMPLE 7

(Confirmation of Detection Limit in a Meat Component-mixed Strain)
Pathogenic *Escherichia coli* O157, *Salmonella* spp. and *Listeria monocytogenes* of Example 1 were used. Each bacterium was inoculated in 10 ml of the above-mentioned medium No. 17, cultured at 35° C. for 18 h, and bacteria culture solution was obtained. Further 225 ml of the medium no. 17 was added to 25 g of minced chicken leg, which was ground with a stomacher for 30 sec and cultured at 35° C. for 18 h. General viable cell counts at that time were $3.1 \times 10^8$ CFU/ml. Culture solution of minced chicken leg was poured by aliquots of 9 ml. Then, 1 ml of 10-fold serial diluted solution of each bacteria culture solution was added to prepare meat sample solution for each diluted series of each bacteria culture solution. After removing large food scraps by passing each sample solution through a 5 μl-filter, as method 1, among DNA extractions of Example 3, the extraction method using Achromopetidase and lysozyme as lytic enzyme was performed, and among the PCR reactions of Example 5, a method using the combination of SEQ ID NOs: 1 to 6 was performed. Further, as method 2, among the DNA extractions of Example 3, the extraction method using Enterolycine and lysozyme was performed, and among the PCR reactions of Example 5, a method using the combination of SEQ ID NOs: 5 to 10 was performed. Each of them was confirmed by 2.5% agarose gel electrophoresis, and the detection limit of pathogenic *Escherichia coli* O157, *Salmonella* spp. and *Listeria monocytogenes* in meat sample solution was confirmed to be $10^3$ CFU/ml, respectively. The electrophoresis figure showing the result of method 1 is shown in FIG. 2 as representative.

EXAMPLE 8

(Detection of Pathogenic Bacteria from Inoculated Food)
Pathogenic *Escherichia coli* O157, *Salmonella* spp. and *Listeria monocytogenes* of Example 1 were used. Each bacterium was inoculated so that each of them becomes $10^2$ CFU/25 g, 10 CFU/25 g, 1 CFU/25 g, $10^{-1}$ CFU/25 g to minced pork meat. Further 225 ml of the medium no. 17 was added to 25 g of inoculated minced pork meat, which was ground with a stomacher for 30 sec and cultured at 35° C. for 24 h. After removing large food scraps by passing each sample solution through a 5 μl-filter, as method 1, among DNA extractions of Example 3, the extraction method using Achromopetidase and lysozyme as lytic enzyme was performed, and among the PCR reactions of Example 5, a method using the combination of SEQ ID NOs: 1 to 6 was performed. Further, as method 2, among the DNA extractions of Example 3, the extraction method using Enterolycine and lysozyme was performed, and among the PCR reactions of Example 5, a method using the combination of SEQ ID NOs: 5 to 10 was performed. Each of the method was confirmed by 2.5% agarose gel electrophoresis. The result of method 1 is shown in FIG. 3 as representative. As a result, it was confirmed that all of the bacteria could be detected with any of the methods, as long as it exists in an amount of 1 CFU/25 g. Harmful pathogenic bacteria such as pathogenic *Escherichia coli* O157, *Salmonella* spp. and *Listeria monocytogenes*, are set up to be "negative" in foods (not included in 25 g), and a comparable or even superior accuracy compared to that of official methods is required for the detection. The present multiple detection method was confirmed to have comparable or even superior accuracy compared to official methods.

EXAMPLE 9

(Comparable Test of Official Methods with the Multiple Detection Method; Detection of Pathogenic Bacteria from Foods on Market)

20 samples including chicken meat and chicken liver were purchased at supermarkets. Inspection of pathogenic *Escherichia coli*, *Salmonella* spp. and *Listeria monocytogenes* were performed by the multiple detection method and the results were compared with those of official methods. Further, the official method was performed as follows.

As for pathogenic *Escherichia coli* O157, 225 ml of novobiocin mEC broth (Kyokuto Pharmaceutical Industrial) was added to 25 g of sample, which was ground with a stomacher for 30 sec, cultured at 42° C. for 18 hours, streaked in CHROMagar O157 medium (Kanto Chemical) and MacConkey Sorbitol Agar medium (Nissui Pharmaceutical), and cultured at 35° C. for 18 to 24 h. Those who showed lilac in CHROMagar O157 medium, and translucent pink in MacConkey Sorbitol Agar medium were determined to be false-positive pathogenic *Escherichia coli* O157, and were streaked in CLIG agar medium (Kyokuto Pharmaceutical Industrial) and cultured at 35° C. for 18 to 24 h. Those whose lower layer was yellow and upper layer was pink, and that were not luminescent to ultraviolet radiation were determined to be false-positive pathogenic *Escherichia coli* O157. They were subjected to indole reaction, and for those being positive (red), agglutination reaction was performed. Agglutination reaction was performed by using the *Escherichia coli* O157 detection kit known as "UNI® kit" (Oxoid). Colonies that were doubtful by agglutination reaction were streaked in CHROMagar O157 medium, MacConkey Sorbitol agar medium, TSI agar medium (Nissui Pharmaceutical) and LIM medium (Nissui Pharmaceutical), and were cultured at 35° C. for 24 hours. Those who showed lilac in CHROMagar O157 medium, translucent pink in MacConkey Sorbitol agar medium, yellow in TSI agar medium and showing no change in LIM medium, were confirmed to be pathogenic *Escherichia coli* O157 by PCR reaction.

As for *Salmonella* spp., 225 g of EEM broth (Nissui Pharmaceutical) was added to 25 g of sample, which was ground with a stomacher for 30 sec. The resultant was cultured at 35° C. for 18 h, and 1 ml thereof was added to 10 ml of Selenite-Cystine base medium (Nissui Pharmaceutical), and cultured at 43° C. for 15 to 18 h. For those wherein the whole or the precipitation showed red, 1-loopful was streaked in MLCB agar medium (Nissui Pharmaceutical) and cultured at 35° C. for 24 h. Those who produced black colonies were determined to be false-positive *Salmonella* spp., and as a confirmation test, these were streaked in TSI agar medium and LIM agar medium. After culturing at 35° C. for 24 to 48 h, those who showed red slope, black in upper layer in TSI medium, and showed no change in LIM medium, were determined to be positive *Salmonella* spp.

As for *Listeria monocytogenes,* 225 ml of UVM *Listeria* selective enrichment bouillon (Merck) was added to 25 g of sample, which was ground with a stomacher for 30 sec. After culturing at 30° C. for 48 h, 1-loopful was streaked in PALCAM *Listeria* selective agar medium (Merck). Those who were determined to be positive *Listeria* after culturing at 35° C. for 48 h, were streaked in horse blood agar medium (Nissui Pharmaceutical), Standard agar medium (Nissui Pharmaceutical) and cultured at 35° C. for 24 to 48 h. Those whose hemolytic was positive, were subjected to oxydase reaction, catalase reaction, gram staining, microscope observation, Api *Listeria* (Japan Biomerieux) and those who were identified as *Listeria monocytogenes* were determined to be positive *Listeria monocytogenes*.

The multiple detection method was performed as follows. 225 ml of medium No. 17 was added to 25 g of sample, which was ground with a stomacher for 30 sec, and cultured at 35° C. for 24 h. After removing large food scraps by passing the culture solution through a 5 µl-filter, as method 1, among DNA extractions of Example 3, the extraction method using Achromopetidase and lysozyme as lytic enzyme was performed, and among the PCR reactions of Example 5, a method using the combination of SEQ ID NOs: 1 to 6 was performed. Further, as method 2, among DNA extractions of Example 3, the extraction method by using Enterolysine and lysozyme as lytic enzyme was performed, and among the PCR reactions of Example 5, a method using the combination of SEQ ID NOs: 5 to 10 was performed. Each of them was confirmed by 2.5% agarose gel electrophoresis. The results are shown in Table 3.

As a result, samples in which pathogenic bacteria were detected were as follows. By the official method: pathogenic *Escherichia coli* O157: 0 sample; *Salmonella* spp.: 3 samples; *Listeria monocytogenes:* 6 samples. By any of the multiple detection method: pathogenic *Escherichia coli* O157: 0 sample; *Salmonella* spp.: 3 samples; *Listeria monocytogenes:* 8 samples. Those who were positive by the official method were all positive by the multiple detection method. Moreover, as for 2 samples of *Listeria monocytogenes* who were negative by the official method and positive by the multiple detection method (Table 3; sample No. 5, 15), the culture solution in No. 17 was streaked and cultured in PALCAM *Listeria* selective agar medium (Merck), and the formed colonies were subjected to an identification test. As a result, they were confirmed to be *Listeria monocytogenes*. From this result, the present multiple detection method was confirmed to have more accuracy compared to the official method.

TABLE 3

| | sample | | General viable cell count (CFU/g) | Official method | | | Multiple detection method | | |
|---|---|---|---|---|---|---|---|---|---|
| | Shop purchased | Name of article | | O157 | Salmonella spp. | Listeria | O157 | Salmonella spp. | Listeria |
| 1 | A | Minced red chicken breast (domestic) | $1.7*10^6$ | neg | neg | neg | neg | neg | neg |
| 2 | | Minced poulet breast fillet (domestic) | $3.7*10^7$ | neg | neg | neg | neg | neg | neg |
| 3 | | Minced poulet leg (domestic) | $2.3*10^7$ | neg | neg | neg | neg | neg | neg |
| 4 | | Poulet liver (domestic) | $3.0*10^5$ | neg | neg | neg | neg | neg | neg |
| 5 | B | Domestic minced poulet fillet | $2.2-10^5$ | neg | pos | neg | neg | pos | pos |
| 6 | | Domestic chopped poulet let (thawed) | $1.7*10^5$ | neg | pos | neg | neg | pos | neg |
| 7 | | Domestic minced poulet breast | $4.9*10^4$ | neg | neg | neg | neg | neg | neg |
| 8 | | Domestic poulet gizzard | $6.0*10^5$ | neg | neg | neg | neg | neg | neg |
| 9 | C | Chicken organs (domestic) | $3.6*10^5$ | neg | pos | neg | neg | pos | neg |
| 10 | | Poulet skin (domestic) | $3.4*10^5$ | neg | neg | pos | neg | neg | pos |
| 11 | | Minced poulet (domestic) | $4.8*10^6$ | neg | neg | neg | neg | neg | neg |
| 12 | | Minced poulet fillet (domestic) | $1.6*10^5$ | neg | neg | neg | neg | neg | neg |
| 13 | D | Thawed chiken heart (domestic) | $8.6*10^6$ | neg | neg | pos | neg | neg | pos |
| 14 | | Thawed poulet cartilage (thawed US fresh products) | $2.7*10^5$ | neg | neg | neg | neg | neg | neg |
| 15 | | Chopped chicken leg (for rice) (domestic) | $1.4*10^6$ | neg | neg | neg | neg | neg | pos |
| 16 | | Poulet leg for fried chicken (S) (product of Brazil) | $6.8*10^7$ | neg | neg | pos | neg | neg | pos |
| 17 | E | Domestic minced poulet | $3.8*10^6$ | neg | neg | neg | neg | neg | neg |
| 18 | | Domestic muscle-removed poulet filet | $1.2*10^4$ | neg | neg | pos | neg | neg | pos |
| 19 | | Domestic chopped poulet | $2.3*10^5$ | neg | neg | pos | neg | neg | pos |
| 20 | | Domestic poulet sparelib | $2.5*10^6$ | neg | neg | pos | neg | neg | pos |
| | | Positive count | | 0 | 3 | 6 | 0 | 3 | 8 |

M: Molecular Weight Marker

Lanes 1 to 7 show the pathogenic *Escherichia coli*-inoculated region (general viable cell counts: $3.1 \times 10^8$ CFU/ml), and the inoculated amount of O157 is as follows:

1: $1.1 \times 10^7$ CFU/ml; 2: $1.1 \times 10^6$ CFU/ml; 3: $1.1 \times 10^5$ CFU/ml; 4: $1.1 \times 10^4$ CFU/ml; 5: $1.1 \times 10^3$ CFU/ml; 6: $1.1 \times 10^2$ CFU/ml; 7: 11 CFU/ml Lanes 8 to 14 show the *Salmonella* spp.-inoculated region (general viable cell counts: $3.1 \times 10^8$ CFU/ml), and the inoculated amount of *Salmonella* spp. is as follows:
8: $5.0 \times 10^6$ CFU/ml; 9: $5.0 \times 10^5$ CFU/ml; 10: $5.0 \times 10^4$ CFU/ml; 11: $5.0 \times 10^3$ CFU/ml; 12: $5.0 \times 10^2$ CFU/ml; 13: 50 CFU/ml; 14: 5 CFU/ml Lanes 15 to 21 show the *Listeria monocytogenes*-inoculated region (general viable cell counts: $3.1 \times 10^8$ CFU/ml), and the inoculated amount of *Listeria monocytogenes* is as follows:
15: $1.1 \times 10^7$ CFU/ml; 16: $1.1 \times 10^6$ CFU/ml; 17: $1.1 \times 10^5$ CFU/ml; 18: $1.1 \times 10^4$ CFU/ml; 19: $1.1 \times 10^3$ CFU/ml; 20: $1.1 \times 10^2$ CFU/ml; 21: 11 CFU/ml

Figure 1:
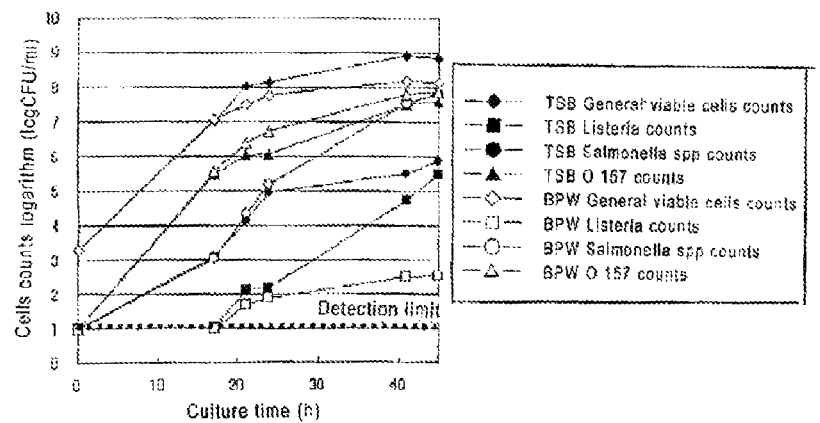
[FIG. 1] It is a figure showing change of the counts of pathogenic *Escherichia coli* O157, *Salmonella* spp., *Listeria monocytogenes* and general viable cells in the culture at 35° C. using Trypto-soya broth (TSB) and Buffered Peptone Water (BPW).
Figure 2:
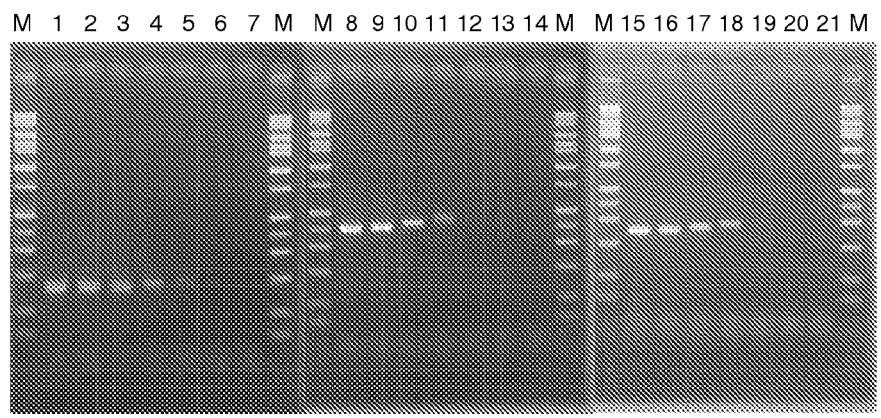
[FIG. 2] It is a figure of the electrophoresis image showing the detection limit by the multiple detection method of each bacterium in the meat sample solution (general viable cell counts: $3.1 \times 10^8$ CFU/ml) inoculated with each bacterium of pathogenic *Escherichia coli* O157, *Salmonella* spp. and *Listeria monocytogenes*.
Figure 3:
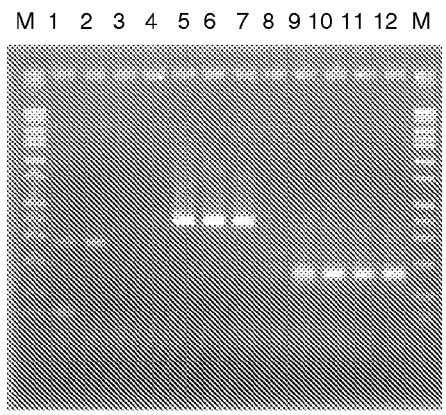

[FIG. 3] It is a figure of the electrophoresis image showing the result of detection of each bacterium by the multiple detection method, using minced pork meat inoculated with pathogenic *Escherichia coli* O157, *Salmonella* spp. and *Listeria monocytogenes*.

M: Molecular Weight Marker

Lanes 1 to 4 show the *Listeria monocytogenes*-inoculated region, and the inoculated amount of *Listeria monocytogenes* is as follows:
1: 16 CFU/25 g; 2: 1.6 CFU/25 g; 3: 0.16 CFU/25 g; 4: 0.02 CFU/25 g Lanes 5 to 8 show the *Salmonella* spp.-inoculated region, and the inoculated amount of *Salmonella* spp. is as follows:
5: 110 CFU/25 g; 6: 11 CFU/25 g; 7: 1.1 CFU/25 g; 8: 0.11 CFU/25 g Lanes 9 to 12 show the pathogenic *Escherichia coli* O157-inoculated region, and the inoculated amount of O157 is as follows:
9: 850 CFU/25 g; 10: 8.5 CFU/25 g; 11: 8.5 CFU/25 g; 12: 0.85 CFU/25 g

The invention claimed is:

1. A method for a high sensitivity multiple microorganism detection which is a method for detecting two or more microorganisms in foods having different properties by culturing the microorganisms in a medium with glucose concentration of 0.15% or less, and/or in a medium with concentration of phosphate-buffer solution of 50 mM or more or in a medium with a buffer capacity equivalent to the concentration of phosphate-buffer solution of 50 mM or more, amplifying a plurality of target genes with a single PCR reaction tube and analyzing the same, consisting of the following steps:

treating at least with a lytic enzyme and/or bacteriocin having lytic activity, a nonionic surfactant and a protein denaturant;

extracting DNA of the target microorganisms to be detected, consisting of removing insoluble fractions by centrifugation, and performing alcohol precipitation; and performing multiplex PCR by mixing a primer specific to the target microorganisms to be detected, wherein, at least one of the two or more microorganisms with different properties is *Listeria monocytogenes*.

2. The method of multiple microorganism detection according to claim 1, wherein a step to culture microorganisms under a culture condition where 1 CFU/100 g microorganisms become $10^3$ CFU/ml or more after 24 h of culture, is included prior to the step of extracting DNA of the target microorganisms to be detected.

3. The method of multiple microorganism detection according to claim 1 or 2, wherein the specific primer is a primer consisting of base sequences shown by SEQ ID Nos: 5 and 6.

4. The method of multiple microorganism detection according to claim 1 or 2, wherein the two or more microorganisms with different properties comprise pathogenic *Escherichia coli* O157.

5. The method of multiple microorganism detection according to claim 4, wherein the specific primer is a primer consisting of base sequences shown by SEQ ID Nos: 1 and 2, or SEQ ID Nos: 7 and 8.

6. The method of multiple microorganism detection according to claim 1 or 2, wherein the two or more microorganisms with different properties comprise *Salmonella* spp.

7. The method of multiple microorganism detection according to claim 6, wherein the specific primer is a primer consisting of base sequences shown by SEQ ID Nos: 3 and 4, or SEQ ID Nos: 9 and 10.

8. The method of multiple microorganism detection according to claim 1 or 2, wherein the microorganisms are cultured in a culture condition where the pH after culture becomes 5.1 or more.

9. The method of multiple microorganism detection according to claim 1 or 2, wherein the extraction is performed after treating with a lytic enzyme and/or bacteriocin having a lytic activity, further treating with a nonionic surfactant and a protein denaturant, removing insoluble fractions by centrifugation, and by depositing DNA by alcohol precipitation.

10. The method of multiple microorganism detection according to claim 1 or 2, wherein the lytic enzyme is Achromopeptidase and/or lysozyme.

11. The method of multiple microorganism detection according to claim 1 or 2, wherein bacteriocin having lytic activity is Enterolysin.

12. The method of multiple microorganism detection according to claim 1 or 2, wherein the nonionic surfactant is ethyleneoxide condensate of sorbitan monolaurate.

13. The method of multiple microorganism detection according to claim 1 or 2, wherein the protein denaturant is Guanidine isothiocyanate.

14. The method of multiple microorganism detection according to claim 1 or 2, wherein Multiplex PCR is performed by combining DNA consisting of base sequences shown by SEQ ID NOs: 1 to 6 at a total concentration of 750 nM or less as a primer.

15. The method of multiple microorganism detection according to claim 1 or 2, wherein Multiplex PCR is performed by combining DNA consisting of base sequences shown by SEQ ID NOs: 5 to 10 at a total concentration of 750 nM or less as a primer.

16. The method of multiple microorganism detection according to claim 1 or 2, wherein the food is edible meat or processed meat product.

17. The method of multiple microorganism detection according to claim 1 or 2, wherein multiplex PCR is performed by combining DNA consisting of base sequences shown by SEQ ID NOs: 5 and 6 at a total concentration of 750 nM or less as a primer.

* * * * *

SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ggcggattag acttcggcta                                                    20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
cgttttggca ctatttgccc                                                    20

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
gggagtccag gttgacggaa aattt                                              25

<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
gtcacggaag aagagaaatc cgtacg                                             26

<210> SEQ ID NO 5
<211> LENGTH: 20
<212> TYPE: DNA
<213> ORGANISM: Artificial Sequence
<220> FEATURE:

<223> OTHER INFORMATION: primer

<400> SEQUENCE: 5
cggaggttcc gcaaaagatg                                          20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
cctccagagt gatcgatgtt                                          20

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
atcattgacg attgtagcac c                                        21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
acatgaggag cattaacttc g                                        21

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gggtcgttct acattgacag                                          20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ttccctttcc agtacgcttc                                          20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gtatttggag acatgggagc                                          20

<210> SEQ ID NO 12

```
<211> LENGTH: 21
<212> TYPE: DNA
<213> ORGANISM: Artificial Sequence
<220> FEATURE:
<223> OTHER INFORMATION: primer

<400> SEQUENCE: 12
actaatgaca cgattcgttc c                                              21

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
cggacagtag ttataccac                                                 19

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
ctgctgtcac agtgacaaa                                                 19

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
agctttggtc gtaaaataag g                                              21

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gatgcccaaa gcagagagat                                                20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
caaactgcta acacagctac t                                              21

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
```

```
gcacttgaat tgctgttatt g                                      21

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
accaatggga tccacaaga                                         19

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
gagctgagct atgtgcgat                                         19

<210> SEQ ID NO 21
<211> LENGTH: 23
<212> TYPE: DNA
<213> ORGANISM: Artificial Sequence
<220> FEATURE:
<223> OTHER INFORMATION: probe

<400> SEQUENCE: 21
cggatgattt gtggcacgag aaa                                    23

<210> SEQ ID NO 22
<211> LENGTH: 26
<212> TYPE: DNA
<213> ORGANISM: Artificial Sequence
<220> FEATURE:
<223> OTHER INFORMATION: probe

<400> SEQUENCE: 22
tctggcatta tcgatcagta ccagcc                                 26

<210> SEQ ID NO 23
<211> LENGTH: 27
<212> TYPE: DNA
<213> ORGANISM: Artificial Sequence
<220> FEATURE:
<223> OTHER INFORMATION: probe

<400> SEQUENCE: 23
agttcaaatc atcgacggca acctcgg                                27
```